(12) United States Patent
Evans et al.

(10) Patent No.: US 8,202,541 B2
(45) Date of Patent: *Jun. 19, 2012

(54) DIETARY SUPPLEMENT COMPOSITION FOR BLOOD LIPID HEALTH

(75) Inventors: David A. Evans, Edmonton (CA); W. Stephen Hill, Ocala, FL (US)

(73) Assignee: U.S. Nutraceuticals, LLC, Eustis, FL (US)

( * ) Notice: Subject to any disclaimer, the term of this patent is extended or adjusted under 35 U.S.C. 154(b) by 635 days.

This patent is subject to a terminal disclaimer.

(21) Appl. No.: 11/671,757

(22) Filed: Feb. 6, 2007

(65) Prior Publication Data

US 2007/0213395 A1 Sep. 13, 2007

Related U.S. Application Data

(60) Provisional application No. 60/771,003, filed on Feb. 7, 2006.

(51) Int. Cl.
*A61K 9/14* (2006.01)
(52) U.S. Cl. .................................... 424/489
(58) Field of Classification Search ............... None
See application file for complete search history.

(56) References Cited

U.S. PATENT DOCUMENTS

| | | | | |
|---|---|---|---|---|
| 5,135,956 A * | 8/1992 | Borg et al. | | 514/724 |
| 5,952,393 A | 9/1999 | Sorkin, Jr. | | 514/729 |
| 6,197,832 B1 | 3/2001 | Sorkin, Jr. | | 514/729 |
| 6,225,354 B1 | 5/2001 | Perez | | 514/724 |
| 6,565,896 B1 | 5/2003 | Gorsek | | 424/655 |
| 6,890,941 B1 | 5/2005 | Angres et al. | | 514/345 |
| 2001/0034338 A1 | 10/2001 | Sorkin, Jr. | | 514/171 |
| 2002/0016314 A1 | 2/2002 | Schersl | | 514/169 |
| 2003/0203854 A1 | 10/2003 | Pischel et al. | | 514/23 |
| 2004/0033202 A1 | 2/2004 | Cooper et al. | | 424/46 |
| 2004/0034241 A1 | 2/2004 | Empie et al. | | 552/540 |
| 2005/0234025 A1 | 10/2005 | Kutney et al. | | 514/171 |
| 2006/0020043 A1 | 1/2006 | Berlin | | 514/724 |
| 2006/0020045 A1 | 1/2006 | Berlin | | 514/724 |
| 2006/0025486 A1 | 2/2006 | Berlin | | 514/724 |
| 2006/0105021 A1 | 5/2006 | Steele et al. | | 424/439 |
| 2006/0198906 A1 | 9/2006 | Majeed et al. | | 424/725 |
| 2007/0166321 A1 | 7/2007 | Villeponteau | | 424/195.16 |
| 2007/0172468 A1 | 7/2007 | Hastings et al. | | 424/94.1 |
| 2008/0260708 A1 | 10/2008 | Hall | | 424/93.45 |

FOREIGN PATENT DOCUMENTS

| | | |
|---|---|---|
| EP | 1108363 | 6/2001 |
| WO | 02/052955 | 7/2002 |
| WO | 03/103632 | 12/2003 |
| WO | WO 03/103632 | * 12/2003 |
| WO | 2005/000041 | 1/2005 |

OTHER PUBLICATIONS

CM. Albert, et al., "*Dietary α-Linolenic Acid Intake and Risk of Sudden Cardiac Death and Coronary Heart Disease,*" American Heart Association, Inc., Circulation, vol. 112, 2005, pp. 3232-3238.
P. Gershkovich et al., "*Uptake of Lipophilic Drugs by Plasma Derived Isolated Chylomicrons: Linear Correlation with Intestinal Lymphatic Bioavailability,*" European Journal of Pharmaceutical Sciences, vol. 26, 2005, pp. 394-404.
M.R. Law et al., "*By How Much and How Quickly Does Reduction in Serum Cholesterol Concentration Lower Risk of Ischemic Heart Disease?*" BMJ Publishing, Feb. 5, 1994, pp. 367-372.
A.J. Lusis, "*Atherosclerosis,*" Nature, vol. 407, Sep. 14, 2000, pp. 233-241.
E. Mantzioris et al., "*Biochmical Effects of a Diet Containing Foods Enriched with N-3 Fatty Acids,*" American Society for Clinical Nutrition, vol. 72, 2000, pp. 42-48.
S.Y. Oh et al., "*Eggs Enriched in ω-3 Fatty Acids and Alterations in Lipid Concentrations in Plasma and Lipoproteins and in Blood Pressure,*" American Society for Clinical Nutrition, vol. 54, 1991, pp. 689-695.
A.P. Simopoulos, "*Essential Fatty Acids in Health and Chronic Disease,*" American Society for Clinical Nutrition, vol. 70 (suppl), 1999, pp. 569S.
J.C. Taylor et al., "*Octacosanol in Human Health*" Nutrition, vol. 19, No. 2, 2003, pp. 192-195.
G. Zhao et al., "*Dietary α-Linolenic Acid Reduces Inflammatory and Lipid Cardiovascular Risk Factors in Hypercholesterolemic Men and Women,*" American Society for Nutritional Sciences, vol. 134, May 21, 2004, pp. 2991-2997.
Database Caplus, Chemical Abstracts Service, Columbus, Ohio, U.S., XP002444837, pp. 1-2 (dated Jul. 30, 2007); entered into STN May 5, 2003.
Database Caplus, Chemical Abstracts Service, Columbus, Ohio, U.S., XP002444838, pp. 1-2 (dated Jul. 30, 2007); entered into STN Apr. 15, 1988.

\* cited by examiner

*Primary Examiner* — Robert A Wax
*Assistant Examiner* — Jeffrey T Palenik
(74) *Attorney, Agent, or Firm* — Allen, Dyer, Doppelt, Milbrath & Gilchrist, P.A.

(57) ABSTRACT

A human or animal dietary supplement composition comprising one or more long chain (C24-C36) primary alcohols (policosanols) dispersed in food-grade oils or fats where the policosanol particle size is substantially less than ten (10) microns. The composition (Nanocosanol™) is effective and convenient for supporting blood lipid health.

11 Claims, No Drawings

DIETARY SUPPLEMENT COMPOSITION FOR BLOOD LIPID HEALTH

RELATED APPLICATION

This application is based upon prior filed provisional application Ser. No. 60/771,003 filed Feb. 7, 2006, the entire subject matter of which is incorporated herein by reference in its entirety.

FIELD OF THE INVENTION

The present invention relates to dietary supplements, and, more particularly to the formulation of such supplements containing fatty alcohols.

BACKGROUND OF THE INVENTION

Cholesterol effects have been studied for years. Examples of research are found in the following references, the disclosures which are hereby incorporated by reference in their entirety.

Albert, C M., K Oh, W Whang, J E Manson, C U Chae, M J Stampfer, W C Willett and F B Hu. 2005. Dietary α-linolenic acid intake and risk of sudden cardiac death and coronary heart disease. *Circulation* 112: 3232-3238.

Castano, G, R Mas, M Arruzazabala et al. 1999. Effects of policcosanol and pravastatin on lipid profile, platelet aggregation and endothelemia in older hyperecholesterolemic patients. *Int J Clin Pharm Res.* 4: 105.

Gershkovich, P, A Hoffman. 2005. Uptake of lipophilic drugs by plasma derived isolated chylomicrons: Linteral corelation with intestinal lymphatic bioavailability. *Eur J Pharm Sci.* 26: 394-404.

Law, M R, N J Wald and S G Thompson. 1994. By how much and how quickly does reduction in serum cholesterol concentration lower risk of ischaemic heart disease? *BMJ* 308: 367-372.

Lusis, A J. 2000. Atherosclerosis. *Nature.* 407: 233-241.

Mantzioris, E., L G Cleland, R A Gibson, M A Neumann, M Demasi and M J James. 2000. Biochmical effects of a diet containing foods enriched with n-3 fatty acids. *Am J Clin Nutr* 72: 42-48.

Mas R. 2000. Policosanol. *Drugs Future.* 25: 569-586.

Oh, S Y, J Ryeu, C Hsieh and D E Bell. 1991. Eggs enriched in ω-3 fatty acids and alterations in lipid concentrations in plasma and lipoproteins and in blood pressure. *Am J Clin Nutr.* 54: 689-695.

Rang, H P, M M Dale and J M Ritter. 1999. *Pharmacology.* 4$^{th}$ ed. Churchill Livingstone, London. 830.

Simopoulos, A P. 1999. Essential fatty acids in health and chronic disease. *Am J Clin Nutr* 70(suppl): 560S-9S.

Taylor, J C, L Rapport and G B Lockwood. 2003. Octacosanol in human health. *Nutrition.* 19: 192-195.

Zhao, G, T D Etherton, K R Martin, S G West, P J Gilles and P M Kris-Etherton. 2004. Dietary α-linolenic acid reduces inflammatory and lipid cardiovascular risk factors in hypercholesterolemic men and women. *J Nutr* 134: 2991-2997.

Cholesterol is an essential component in the body and used in cell membranes. Excessive levels, however, can lead to hypercholesterolemia and atherosclerosis, which can result in coronary heart disease. Cholesterol is transported via: high-, low-, intermediate-, and very low-density lipoproteins; chylomicron remants; and chylomicrons. High levels of high-density lipoproteins are desirable because they transport cholesterol from the peripheral tissues to the liver, thereby maintaining cholesterol homeostasis. The main transport mechanism, however, is low-density lipoprotein, which moves cholesterol in the blood plasma and incorporates it into cell membranes. Increased levels of low-density lipoprotein, however, can interfere with uptake binding mechanisms.

Statin drugs such as atorvastatin, fluvastatin, pravastatin and simvastatin are often administered to those suffering from cholesterol issues. These drugs inhibit competitively 3-hydroxy-3-methylglutaryl coenzyme A reductase, thereby reducing cholesterol synthesis. Side effects of statins can include myositis, headache, rash, angioedema, gastrointestinal effects and altered liver functions. In addition, these drugs should not be used in patients with renal failure or in people with compromised liver function (Taylor et al. 2003).

Dietary fatty acid intake can influence many health factors, but much interest has been placed on the n-3 (omega-3) fatty acids. These essential fatty acids include α-linolenic (ALA), eicosapentaenoic (EPA) and docosahexaenoic acid (DHA). Various studies have shown that n-3 fatty acids are essential for normal growth and development. They may also play a critical role in the prevention and treatment of coronary heart disease, hypertension, diabetes and other inflammatory and autoimmune disorders (Simopoulos 1999). ALA is present in certain vegetable oils (flaxseed, cranberry seed, canola and chia) whereas EPA and DHA are found in fish, fish oil and algae products.

Between ethnic dietary groups it has been shown that the higher ratio of n-6 to n-3 in thrombocyte phospholipids can be a cause for a higher death rate from cardiovascular disease. This increased ratio also results in increased rates of type 2 diabetes, of which atherosclerosis is a major complication (Weber, 1991). Achieving target levels of n-3 fatty acids can be difficult with modern western diets deficient in ALA, EPA and DRA, and excessive in the n-6 linoleic acid. Target tissue concentrations for ALA and EPA can be met with consumption of ALA (Mantzioris et al. 2000). A primary cardiovascular benefit from n-3 fatty acid ingestion can be reduced blood clotting in vessel walls and reduced ventricular arrhythmias, (Zhao et al. (2004)). Some studies have found a dose-response relation between n-3 intake and beneficial effects on cardiovascular disease risk factors. Some studies have shown an inverse relationship between ALA intake and risk of sudden cardiac death (Albert et al. (2005)).

Policosanols can be defined as a mixture of long chain (C24-C36) aliphatic primary alcohols, which are commonly derived from sugar cane, rice bran, beeswax, wheat or sorghum. Predominant alcohols in this group are tetracosanol, hexacosanol, octacosanol and triacontanol.

Policosanols can lower cholesterol levels by inhibiting cholesterol biosynthesis via downregulation of 3-hydroxy-3-methylglutaryl Coenzyme A enzyme expression (Menendez et al. 1994, McCarty 2002). A study by Hernandez et al. (1992) found a reduction in serum cholesterol levels of subjects taking 20 mg policosanol per day for 4 weeks. Significant decreases in LDL levels, with increased levels of HDL were also noticed. Another double-blind randomized study by Castano, et al. (1999) investigated the effects of policosanol and pravastatin on the lipid profile in older hypercholesterelemic patients. Policosanol was found to increase HDL levels, but was also more effective than pravastatin in lowering LDL levels and the LDL:HDL ratio.

Policosanols can also protect lipoproteins from peroxidation, in both lipid and protein moieties (Menendez et al. 1999). This can be an important effect, since LDL oxidation is thought to be a necessary step in the development of atherosclerosis.

Policocanols may provide fewer side effects than statins, increase HDL cholesterol levels and have a reduced cost (Taylor et al. 2003).

One issue with policosanols are poor solubility, and difficulty with absorbtion in the gut. Human studies with [$^3$H]-octacosanol showed the majority (81-91%) of total radioactivity was excreted in the feces, and only 1.2% of total radioactivity was found in urine (Mas, 2000).

Reducing the particle size of poorly solube compounds such as policosanol to a micron or sub-micron range, improved absorbtion and bioavailability is desirable.

SUMMARY OF THE INVENTION

A human or animal dietary supplement composition comprises a blood lipid health-effective amount of one or more long chain (C24-C36) primary alcohols (policosanols) dispersed in one or more food-grade fats or oils, wherein the particle sizes of the alcohols are substantially less than 10 microns.

The particle sizes of the alcohols can be substantially greater than 0.2 microns and substantially less than 5.0 microns. The alcohols can be selected from one of at least octacosanol, triacontanol and hexacosanol. The alcohols can also be derived from natural sources, including rice bran, beeswax, sugar cane, sorghum or wheat.

In another aspect, the food-grade fats or oils contain one of at least:

(a) not less than twenty five percent (25%) by weight of polyunsaturated fatty acids;

(b) not less than ten percent (10%) by weight of omega-3 fatty acids;

(c) not less than two and one-half percent (2.5%) by weight of squalene; and (d) not less than eight fifty parts per million (850 ppm) by weight of tocopherols and tocotrienols in total.

The food-grade fats or oils could include at least one of cranberry seed oil, amaranth seed oil, fish and marine/algal oils, safflower oil, sunflower seed oil, soybean oil, canola oil, olive oil, linseed oil, flax oil, hemp oil, borage oil, evening primrose oil, chia oil and hibiscus oil.

In yet another aspect, the policosanols include about 0.1 percent by weight of the fats or oils to about 6.0 percent by weight of the fats or oils. The policosanols could also include about 0.5% by weight of the fats or oils to about 5.0% by weight of the fats or oils, or from about 1.0% by weight of the fats or oils to about 5.0% by weight of the fats or oils.

The composition could be formed from biologically active extracts and compounds, including vitamins, minerals, antioxidants, carotenoids, tocopherols, tocotrienols, phytosterols, polyphenols, polysaccharides and bioflavonoids.

A vehicle for the composition could be an emulsion, solution, dispersion, cream, tablet, capsules and powder. A vehicle for carrying the composition could be food, feed or beverage.

A method aspect is also set forth.

DETAILED DESCRIPTION OF THE PREFERRED EMBODIMENTS

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

The natural dietary supplement industry represents a $300 billion dollar marketplace worldwide. Many natural botanical materials and extracts have been used by mankind for health purposes for thousands of years. In some parts of the world, natural health products are preferred over chemical or pharmaceutical ones due to reasons of religion, culture, safety, cost and demonstrated efficacy.

Among the botanical products that have a history of use in support of human blood lipid health are certain fatty alcohols derived from botanical waxes, for example, sugar cane wax, rice bran and other cereal waxes and bees wax. The most important of these are the long chain (C24-C36) primary alcohols, octacosanol, triacontanol and hexacosanol.

Policosanols, as noted above, are known to have a number of beneficial effects on blood lipid health. These beneficial effects include lowering blood cholesterol levels, reducing Low Density Lipoproteins (LDL), increasing High Density Lipoproteins (HDL) and reducing blood triglycerides.

Some difficulties have been experienced in using policosanols to improve blood lipid health. For example, these fatty alcohols are poorly soluble in lipid carriers and completely insoluble in aqueous carriers. This greatly reduces their availability in the digestive tract. Normal digestion of fats and oils in the mammalian diet is achieved by emulsification with bile salts and phospholipids followed by direct adsorption of the resulting chylomicrons through the gut wall. Typical chylomicron sizes are 0.5 microns to 2 microns.

Modern emulsification technology (nanotechnology) now makes it possible to produce dispersed particle sizes in liquid carriers into the 1 micron size. As noted above, many different physical emulsification techniques are available.

In accordance with a non-limiting example of the present invention, one or more of these technologies is used to prepare a dietary supplement composition in which the policosanol particle sizes are substantially less than 10 micron range within an acceptable oil carrier (Nanocosanol™). The composition may include the use of food-grade emulsifiers, for example, polysorbates, lecithin, hydrolyzed lecithin, mono- and di-glycerides, and acylated mono- and di-glycerides. The presence of the emulsifiers inhibits the tendency of the particles to adhere under electrostatic attractive forces. Such a composition has the advantage of increased digestibility and stability on storage.

In one aspect, the composition includes the selection of an oil carrier with beneficial blood lipid properties. Such fats and oils may include polyunsaturated fatty acids, omega-3 fatty acids, squalene, phytosterols, tocopherols and tocotrienols. Typical fats and oils include, for example, fish oils, shark liver oil, cranberry seed oil, amaranth seed oil, sunflower seed oil, linseed oil, chia oil and evening primrose seed oil.

In another aspect, the composition optimizes the balanced intake of both policosanols and the beneficial lipid carrier. By suitable selection of the ratio of the carrier oil to the policosanols, it is possible to produce the composition such that preferred intakes of both policosanols and the beneficial lipid can be conveniently administered in acceptable unit and daily doses.

Such a composition as (Nanocosanol™) can be used to promote and support blood lipid health. Daily intake of such composition, in the preferred dose range, will provide the subject with the desired daily intakes of policosanols and lipid carrier, resulting in improved blood lipid profiles. This can include, for example, lower cholesterol, lower triglycerides, lower Low Density Lipoprotein (LDL) and higher High Density Lipoprotein (HDL).

In accordance with one aspect of the present invention, a dietary supplement composition is disclosed (Nanocosanol™) in which poorly soluble policosanols are dispersed in food-grade oils or fats, in which the policosanol particle sizes in the composition are substantially less than 10 microns and preferably in the range of from about 0.2 microns to about 5.0 microns.

In accordance with another aspect of the present invention, the body's absorption and utilization of the policosanols from the composition is substantially enhanced as compared with the absorption and utilization of policosanols administered in solid or tablet form. The policosanol dispersion of the composition is stable on storage and does not separate from the lipid carrier.

The disclosed lipid carrier used in the composition may be selected from a group of oils and or fats that are known to have beneficial effects on blood lipid health. Such beneficial lipids, for example, may contain one or more of polyunsaturated fatty acids, phytosterols, omega-3 fatty acids, squalene, tocopherols and tocotrienols.

The concentration of policosanols of the composition optimizes the daily intake of both policosanols and the beneficial lipid carrier. The preferred daily intake of policosanols can be about 20-30 mg per day for an adult. The preferred daily intake for beneficial lipids, however, is often as high as from about 500 mg to 5,000 mg per day for an adult. The weight of policosanols in the disclosed composition is from about 0.3 percent by weight of beneficial lipid to about 5.0 percent by weight of beneficial lipid. Such a disclosed composition allows the ratio of beneficial lipid to policosanols to range from about 333:1 to about 20:1. This ratio ensures that a policosanol intake of about 25 mg per day is always in combination with from about 500 mg per day to about 5,000 mg per day of the beneficial lipid. The disclosed composition allows delivery of a preferred daily dose of both policosanols and beneficial lipid in a single formulation.

It will be understood by those in the art that liquid dietary supplement daily doses of from about 500 mg to about 5,000 mg can be conveniently delivered in capsules from about 500 mg to about 1,000 mg. For example, a three percent dispersion of policosanols in a beneficial lipid can conveniently supply 24 mg of policosanols per day together with 800 mg of beneficial lipid, when taken as two 400 mg capsules daily.

It will be understood by those in the art that such a composition, in capsule or liquid form, may be conveniently supplemented with other biologically active extracts and compounds, including, for example, vitamins, minerals, antioxidants, carotenoids, tocopherols, tocotrienols, phytosterols, fatty alcohols, polysaccharides and bioflavonoids.

The disclosed dietary supplement composition (Nanocosanol™) is a novel, improved, more efficient vehicle for the administration of policosanols in support of blood lipid health. It is effective in lowering the blood serum cholesterol level of both normal and hypercholesterolemic subjects.

The following examples are illustrative of the present invention, and are not to be construed as limiting thereof.

EXAMPLE 1

Supercritical $CO_2$ Extracts of Cranberry (*Vaccinium macrocarpon*) Seed, Amaranth (*Amaranthus hypochondriacus*) Seed and Rice (*Oryza sativa*) bran wax were individually manufactured in a commercial 150 liter extraction unit. Within a heated vessel, the policosanol containing rice bran wax extract was dissolved into a mixture of cranberry and amaranth seed oily extracts at 65° C. After cooling to ambient temperature, soybean lecithin was combined. This resultant formulation was processed in a high pressure homogenization unit to obtain a stable dispersion of rice bran wax. The homogenizer is designed to produce high rates of shear and cavitation. Using light microscopy, average particle size was determined. Composition of the dispersion was as follows:

Policosanols: 1.45%, average particle size 0.3-2.6 μm.
alpha-Linolenic acid: 13.2%
Squalene: 3%
Tocopherols: 499 μg/g
Tocotrienols: 709 μg/g
Phytosterols: 4.4 mg/g

EXAMPLE 2

The Nanocosanol formulation from Example 1 was encapsulated in standard gelatin softgels by a third party manufacturer. Softgels were 690 mg nominal fill weight and each contained 10 mg policosanol, 21 mg squalene, 91 mg n-3 fatty acids (alpha-linolenic), 3.0 mg phytosterols, 489 μg tocotrienols and 344 μg tocopherols.

EXAMPLE 3

Nanocosanol™ softgels, manufactured according to Example 2 were administered to 11 subjects over an approximately 3-month period. The study was a non-placebo placebo controlled open label trial and used volunteers with normal and modestly elevated levels of serum cholesterol. Starting point individual cholesterol levels ranged from about 140 to about 258. Dosage was 2×600 mg capsules per day providing 20 mg per day of policosanols together with 1200 mg per day of a 50:50 mixture of Cranberry and Amaranth Seed oils. In addition to the Policosonols, the Nanocosanol™ formulation provided tocopherols, tocotrienols, omega-6 and omega-3 fatty acids, polyunsaturated fatty acids and squalene.

Subject blood samples were taken by an independent clinic at 0 (Base), 30, 60 and 90 days. The blood samples were subjected to Blood Lipid by an authorized independent laboratory.

Variables measured were Triglycerides, Cholesterol, LDL Cholesterol and HDL Cholesterol.

All data were expressed as a difference (change) from the Base level for that subject and that variable. One subject did not complete a blood sample at 90 days so the total number of observations was 32 (11, 11, 10). Analyses were based the combined data over all three periods. The mean changes for the Blood Lipid variables were:

| Triglycerides | −4.72% | p = 0.175 |
| LDL Chol. | −10.06% | p = 0.125 |
| HDL Chol. | +1.85% | p = 0.175 |
| OTHER Chol. | −5.23% | p = 0.125 |
| Chol. | −5.96% | p = 0.050 |
| LDL/HDL | −11.73% | p = 0.050 |
| Chol/HDL | −7.43% | p = 0.050 |

The Cholesterol reduction of 5.96% was significant at the 5% level of probability using the One-Sided t-test with 31 DF, as were the LDL/HDL ratio and the Chol/HDL ratio. The other Blood Lipid decreases are not significant at the 5% Level but have only a 1 in 6 to about 1 in 8 chance of occurring by chance.

Analysis of Covariance was used to estimate the linear regression of variable change on variable Base level. Both the pooled within period regression coefficient and the overall regression coefficient for most variables were negative, highly significant at the 1% level (1 and 30 DF) and virtually identical.

Using the estimated regression equation, an estimate of the variable reduction resulting from a "typical high-quartile" Base level was calculated for each variable. These are shown as follows:

| | | | | | |
|---|---|---|---|---|---|
| Triglyceride | b = −0.2918 | p < 0.010 | Base = 200 | Chng = −29.92 | (−14.62%) |
| LDL | b = −0.8234 | p < 0.010 | Base = 150 | Chng = −34.34 | (−22.89%) |
| HDL | b = +0.0854 | p = 0.175 | | | |
| OTHER Chol | b = −0.2870 | p < 0.010 | Base = 35 | Chng = −4.43 | (−12.66%) |
| Chol | b = −0.7704 | p < 0.010 | Base = 225 | Chng = −24.27 | (−10.78%) |
| LDL/HDL | b = −0.4534 | p < 0.010 | Base = 2.75 | Chng = −0.52 | (−18.89%) |
| Chol/HDL | b = −0.3577 | p < 0.010 | Base = 5.00 | Chng = −0.78 | (−15.52%) |

It can be seen from the resulting data that the Nanocosanol™ treatment resulted in significant and near significant reductions over base level for all Blood Lipid variables except HDL which showed a small increase. Nanocosanol™ was clearly and demonstrably responsible for a significant improvement in Blood Lipid health. This is most clearly established for Total Cholesterol and the critical LDL/HDL and Chol/HDL ratios. It is also likely that in a larger sample size, the reductions in Triglycerides and LDL and the increase in HDL, both desirable treatment effects, would be confirmed as significant.

It is also clear from the regression analysis that decreases in Blood Lipid values are a function of the Base level. These results suggest that for those subjects in the population with highly elevated serum cholesterol values, Nanocosanol™ has the potential to bring about 15%-20% reductions.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A human or animal dietary supplement composition comprising a blood lipid health-effective amount of one or more long chain (C24-C36) primary alcohols comprising policosanols, dispersed in food-grade fats or oils, wherein the particle sizes of the alcohols are greater than 2.6 microns and less than 10 microns, wherein the food-grade fats or oils comprise:
  (a) not less than twenty five percent (25%) by weight of polyunsaturated fatty acids;
  (b) not less than ten percent (10%) by weight of omega-3 fatty acids;
  (c) not less than eight-hundred fifty parts per million (850 ppm) by weight of tocopherols and tocotrienols in total; and
  wherein the policosanols comprise from about 0.1 percent by weight of the fats or oils to about 6.0 percent by weight of the fats or oils, and further comprising a food-grade emulsifier.

2. The composition of claim 1, wherein the particle sizes of the alcohols are greater than 2.6 microns and less than 5.0 microns.

3. The composition of claim 1, wherein the alcohols are selected from at least one of octacosanol, triacontanol and hexacosanol.

4. The composition of claim 1, wherein the alcohols are selected from natural sources comprising at least one of rice bran, beeswax, sugar cane, sorghum and wheat.

5. The composition of claim 1, wherein the food-grade fats or oils comprise at least one of cranberry seed oil, amaranth seed oil, fish and marine/algal oils, safflower oil, sunflower seed oil, soybean oil, canola oil, olive oil, linseed oil, flax oil, hemp oil, borage oil, evening primrose oil, chia oil and hibiscus oil.

6. The composition of claim 1, wherein the policosanols comprise from about 0.5% by weight of the fats or oils to about 5.0% by weight of the fats or oils.

7. The composition of claim 1, wherein the policosanols comprise from about 1.0% by weight of the fats or oils to about 5.0% by weight of the fats or oils.

8. The composition of claim 1, and further comprising biologically active extracts and compounds, including at least one of carotenoids, phytosterols, polyphenols, polysaccharides and bioflavonoids.

9. The composition of claim 1, and further comprising a delivery vehicle as an emulsion, solution, dispersion, cream, tablet, capsules or powder.

10. The composition of claim 1, and further comprising a delivery vehicle for carrying the composition comprising food, feed or beverage.

11. The composition of claim 1, further comprising squalene.

* * * * *